US008852881B2

(12) United States Patent
Negulescu et al.

(10) Patent No.: US 8,852,881 B2
(45) Date of Patent: Oct. 7, 2014

(54) MULTIWELL ASSAY APPARATUS AND METHOD FOR DETERMINING BIOLOGICAL ACTIVITY OF COMPOUNDS

(75) Inventors: Paul A. Negulescu, Del Mar, CA (US); Alec T. Harootunian, San Diego, CA (US); Philip E. Salzmann, Cardiff, CA (US); Javier H. Flores, San Diego, CA (US); James E. Sinclair, Carlsbad, CA (US); Minh Vuong, San Diego, CA (US); Ashvani K. Singh, San Diego, CA (US); Fred F. VanGoor, San Diego, CA (US)

(73) Assignee: Vertex Pharmaceuticals, Inc., Cambridge, MA (US)

( * ) Notice: Subject to any disclaimer, the term of this patent is extended or adjusted under 35 U.S.C. 154(b) by 1956 days.

(21) Appl. No.: 11/605,814

(22) Filed: Nov. 29, 2006

(65) Prior Publication Data

US 2007/0072257 A1 Mar. 29, 2007

Related U.S. Application Data

(62) Division of application No. 10/815,176, filed on Mar. 31, 2004, now Pat. No. 7,169,609.

(51) Int. Cl.

| | |
|---|---|
| ***C12Q 1/02*** | (2006.01) |
| ***C12N 11/00*** | (2006.01) |
| ***C12M 1/34*** | (2006.01) |
| ***C12M 3/00*** | (2006.01) |
| ***C12N 5/07*** | (2010.01) |
| *B01L 3/00* | (2006.01) |

(52) U.S. Cl.

CPC ........... *B01L 3/5085* (2013.01); *B01L 3/50255* (2013.01); *B01L 2300/0829* (2013.01); *B01L 2300/0645* (2013.01)

USPC ....... 435/29; 435/174; 435/287.1; 435/288.4; 435/297.1; 435/297.5; 435/395; 204/403.06

(58) Field of Classification Search

CPC .......... C12Q 1/02; C12Q 1/025; C12N 11/00; C12N 5/06; C12M 1/34; C12M 1/3407; C12M 3/00

See application file for complete search history.

(56) References Cited

U.S. PATENT DOCUMENTS

| | | | | |
|---|---|---|---|---|
| 4,055,799 | A | 10/1977 | Coster et al. | |
| 5,459,068 | A * | 10/1995 | Madara | 435/287.1 |
| 5,643,742 | A | 7/1997 | Malin et al. | |
| 5,738,826 | A | 4/1998 | Lloyd | |
| 5,972,694 | A | 10/1999 | Mathius | |
| 6,488,829 | B1 | 12/2002 | Schroeder et al. | |
| 6,936,462 | B1 | 8/2005 | Owen et al. | |
| 7,524,517 | B2 * | 4/2009 | Schwiebert et al. | 424/641 |
| 7,582,424 | B2 * | 9/2009 | Trucksis | 435/6 |
| 2002/0195337 | A1 | 12/2002 | Osipchuk et al. | |

FOREIGN PATENT DOCUMENTS

| | | | |
|---|---|---|---|
| DE | 100 08 373 | A1 | 9/2001 |
| DE | 101 17 723 | A1 | 10/2002 |
| EP | 1271 144 | A1 | 1/2003 |
| FR | 2 844 052 | A1 | 3/2004 |
| WO | WO 94/28111 | | 12/1994 |
| WO | WO 96 02627 | A1 | 2/1996 |
| WO | WO 99/66329 | | 12/1999 |
| WO | WO 03/085484 | A2 | 10/2003 |

OTHER PUBLICATIONS

Corning, "Transwell Permeable Supports", (2003) Coring Incorporated, pp. 1-12.
H.H. Zerahn K. "Active Transport of Sodium as the Source of Electric Current in the Short-Circuited Frog Skin", (1951), Acta Physical Scand. 23: 110-127.
Sigworth F. J.: "Design of the EPC-9, A Computer-Controlled Patch-Clamp Amplifier 1. Hardware", Journal of Neuroscience Methods, Elsevier Science Publisher B.V., Amsterdam, vol. 56, No. 2., Feb. 1, 1995, pp. 195-202.
International Search Report dated Feb. 2, 2011.

* cited by examiner

*Primary Examiner* — David M Naff

(74) *Attorney, Agent, or Firm* — Knobbe Martens Olson & Bear, LLP

(57) ABSTRACT

A device for characterizing the biological properties of cells can include a plurality of dual-compartment assay chambers wherein the compartments of each chamber are separated by a cell layer across which ions can flow. The biological properties of the cell layer in the presence or absence of experimental compounds can be determined by measuring an electrical gradient across the layer. A individual dual-compartment chamber of this type may be referred to as an "Ussing chamber."

7 Claims, 11 Drawing Sheets

MULTIWELL ASSAY APPARATUS AND METHOD FOR DETERMINING BIOLOGICAL ACTIVITY OF COMPOUNDS

CROSS REFERENCE TO RELATED APPLICATION

This application is a divisional of U.S. application Ser. No. 10/815,176, entitled "MULTIWELL PLATE ASSEMBLY FOR USE IN HIGH THROUGHPUT ASSAYS" and filed on Mar. 31, 2004, now U.S. Pat. No. 7,169,609, which is incorporated by reference in its entirety.

BACKGROUND OF THE INVENTION

1. Field of the Invention

The present invention relates generally to instrumentation and methods for manipulating and studying electrical properties of epithelial cells, intact biological membranes, and tissues.

2. Description of the Related Art

The Ussing chamber is named after Hans H. Ussing, who pioneered the concept of measuring ion flux across epithelial tissues via electrical measurements in the 1950s. See Ussing, H. H. & Zerahn, K. (1951) Active transport of sodium as the source of electric current in the short-circuited isolated frog skin. *Acta Physiol. Scand.* 23: 110-127, hereby expressly incorporated by reference in its entirety.

Ussing's original studies used intact frog skin, but over the years, the Ussing chamber has become a preferred tool to study transport across a variety of epithelial cells, intact biological membranes, and tissues. More recently, progress has been made in the ability to grow primary epithelial cells or immortalized cell lines on a porous supporting membrane. Under appropriate culture conditions, these cells grow to confluence, establish polarity, and can form tight junctions between cells, creating a high resistance monolayer (ca. ≥0.3 kohm/cm$^2$) suitable for transepithelial measurements. The ability to use primary cells or engineered cell lines allows the biophysical and pharmacological study of epithelial function, including effects on ion channels or transporters. Despite its utility and diverse applications, the experiments remain laborious and time-consuming. This limits the utility of this technique for modern research methods, including screening of molecules or proteins for effects on ion transport.

A typical Ussing chamber is shown in FIG. 1. As shown, this Ussing chamber consists of three main parts: a first compartment, a second compartment, and a middle insert that carries the membrane on which the cell layer resides. The first compartment 10 is separated from a second compartment 12 by the middle insert 14. The middle insert 14 contains a membrane support 16 on which a confluent epithelial cell layer 18 has been grown. The cells of the cell layer are held together by tight junctions. The cell layer effectively prevents molecules from traveling between the first and second compartments unless such a molecule passes through one of the cells by entering through a cellular channel located on side of the cell and then exiting the cell through a cellular channel located on the other side of the cell. Often, one ionic component of the salt in one compartment is higher than in the other and the ionic flux down the concentration gradient is measured, although this is not required. This flux provides information on the channels or transporters in the cell membrane. In this example, the first compartment has a higher KCl concentration than the second compartment. A chloride ion flux is thus produced by chloride ions passing through the cells of the cell layer 18.

FIG. 2 shows the use of a voltage clamp to help measure this flux. In this specific example, as $Cl^-$ ions move down the concentration gradient, the potential becomes more negative in the second compartment 12. This potential change is sensed by voltage electrodes 20 and used by the servo loop to command a charge injection via the charge injection or current electrodes 22. In this way, the potential change is "short-circuited" and the voltage across the cell layer remains "clamped" at a constant level. The amount of charge injected is equal to the amount of $Cl^-$ that moves across the cell layer, which allows the $Cl^-$ flux to be measured. The electronics responsible for pumping this charge can also report it to an external data acquisition system. Both voltage and current electrodes in this arrangement are silver/silver chloride (Ag/AgCl) encased in plastic pipettes 24 filled with KCl/agar 26 (10% agar in 1 M KCl). Such compound electrodes are advantageous because sometimes the chloride concentrations in one or both compartments are modified during the experiment by addition of reagents or solutions. The KCl/agar provides a constant $Cl^-$ environment surrounding the Ag/AgCl so that chloride concentrations changes in the bath do not cause voltage jumps. In the current state of the art, the voltage clamping electronics are typically fitted with a manual user interface which includes a complicated assortment of knobs, switches, and dials through which the user enters all parameters needed to set up the experiment. As for the chamber itself, it is typically made out of machined and polished Plexiglas and its dimensions are usually about 3×6×7 cm. Typically, each compartment's volume is about 5 mL, but the minimum workable volume is about 3 mL. Cells can be grown on a Snapwell™ plate, which is available from Corning Costar (Cambridge, Mass.). A Snapwell™ plate typically contains six wells, each with a polycarbonate membrane support on which a cell layer can be grown. Once confluence is reached, one Snapwell™ support is removed and installed into the insert, which is then mounted between the two halves of the Ussing chamber. The area of the microporous membrane support on each Snapwell™ is typically about 1.1 cm$^2$.

As described above, the typical Ussing chamber experiment is a time-consuming, cumbersome, and labor-intensive process which includes (1) zeroing the electrodes to compensate for the solution resistance, (2) mounting one Snapwell™ on the insert, (3) installing the insert into the chamber, (4) inserting the electrodes, (5) adding solutions and reagents, (6) manipulating the electronics manual interface, and (7) collecting the data. Silver/silver chloride electrodes also wear out, and rebuilding these compound electrodes usually involves a cumbersome process of handling melted agar. A typical Ussing experiment takes several hours, yet provides only one data set, as only one Snapwell™ can be tested at a time. In the context of drug screening, where it is often desirable to screen hundreds or thousands of compounds, such throughput is unacceptably low. Even in the scenario of a secondary screen, or the profiling of medicinal chemistry compounds, this throughput of one data point in several hours is still too low to satisfy the need to test a number of compounds at various concentrations in order to calculate an effective concentration, for example, when obtaining a dose response profile. What is needed in the art is a Ussing chamber apparatus and method for its use that allows greater throughput.

SUMMARY OF THE INVENTION

One aspect of the invention is a multiwell plate assembly containing: a first tray containing an array of sample wells, wherein each sample well contains an electrode having an electrical connection that passes through an opening in a wall of the sample well; a second tray containing a plurality of cell layers such that the second tray can be coupled to the first tray to form a plurality of assay chambers such that each assay chamber contains: a first compartment; a second compartment; and at least one intact or permeabilized cell layer separating the first compartment from the second compartment.

Another aspect of the invention is a method of forming a multiwell plate assembly including: providing a first tray containing a plurality of sample wells, each sample well of the plurality of sample wells containing one or more electrodes; and substantially simultaneously placing a plurality of cell layers into the plurality of sample wells.

Another aspect of the invention is a method of characterizing the biological activity of a candidate compound including: placing a first tray of a plurality of wells having cell layers affixed to the wells into a second tray of a plurality of wells with electrodes mounted therein such that the trays form respective pairs of compartments separated by the cell layers; placing electrodes in the plurality of wells of the first tray; exposing one or more cells of the layer of cells to the candidate compound; monitoring an electrical property with the electrodes wherein the property is indicative of a biological activity of the compound.

Another aspect of the invention is an assay apparatus containing a multiwell plate having a plurality of wells, each well having a top opening and a bottom panel, wherein at least some of the wells have one or more other openings in the bottom panel.

Another aspect of the invention is an assay apparatus containing: a first multiwell plate having a plurality of wells, each well having a top opening and a bottom panel; a second multiwell plate having a plurality of wells that are aligned with the plurality of wells of the first multiwell plate and are dimensioned such that the plurality of wells on the second multiwell plate fit into the top openings of the plurality of wells of the first multiwell plate to create dual-compartment wells; a first set of electrodes extending into the plurality of wells of the first multiwell plate; and a second set of electrodes extending into the plurality of wells of the second multiwell plate.

Another aspect of the invention is a multiwell assay apparatus containing: a pair of adjacent multiwell plates positioned relative to each other to form a plurality of dual-compartment wells; a pair of printed circuit boards sandwiching the pair of adjacent multiwell plates; and electrodes extending from each of the printed circuit boards and into at least some of the dual-compartment wells.

Another aspect of the invention is a multi-channel voltage clamp for a plurality of dual-compartment assays, the multi-channel voltage clamp containing: a plurality of voltage sensors coupled to corresponding ones of the plurality of dual-compartment assays, each voltage sensor having an output dependent on a voltage difference between the different compartments of the dual-compartment assays to which each voltage sensor is coupled; a digitally programmable controller receiving as inputs a plurality of signals, each of the signals dependent on a corresponding voltage sensor, the programmable controller also providing a plurality of outputs; a plurality of servo amplifiers, each servo amplifier receiving a first signal dependent on the output of a corresponding voltage sensor and a second signal dependent on one of the programmable controller outputs; wherein each servo amplifier is configured to produce an output dependent on changes in the voltage difference between the different compartments of a corresponding dual-compartment assays.

Another aspect of the invention is an assay apparatus containing: a regular array of dual-compartment assays; a corresponding regular array of electrodes extending into both compartments of the dual-compartment assays; multi-channel digitally programmable electronic control and sensing circuitry configured to substantially simultaneously apply signals to at least some of the electrodes and sense signals from at least some of the electrodes.

DETAILED DESCRIPTION OF THE PREFERRED EMBODIMENT

Multi-well plates (or trays) are widely used in experiments in which it is desirable to perform numerous assays in parallel.

Some embodiments of the present invention include an array of Ussing chambers. Some embodiments feature a first multiwell plate having a plurality of wells and a second multiwell plate having a plurality of wells wherein the plates are dimensioned so that the wells of the second plate can be aligned and placed into the wells of the first plate so as to create dual-compartment wells;

In some advantageous embodiments, an array of Ussing chambers is designed using commercially available multiwell plates that have been modified in certain ways described more fully below. Various improvements to electronics and electrode design are also included in some embodiments of the present invention. By conducting experiments in parallel and reducing the number of individual chambers that need to be handled, some embodiments of the invention can increase the throughput and simplify the execution of transepithelial measurements from cell cultures. In some embodiments, a Ussing chamber array is interfaced with liquid handling hardware, electronic controls, and/or software to allow experimental manipulation and/or data analysis.

Figure 1:
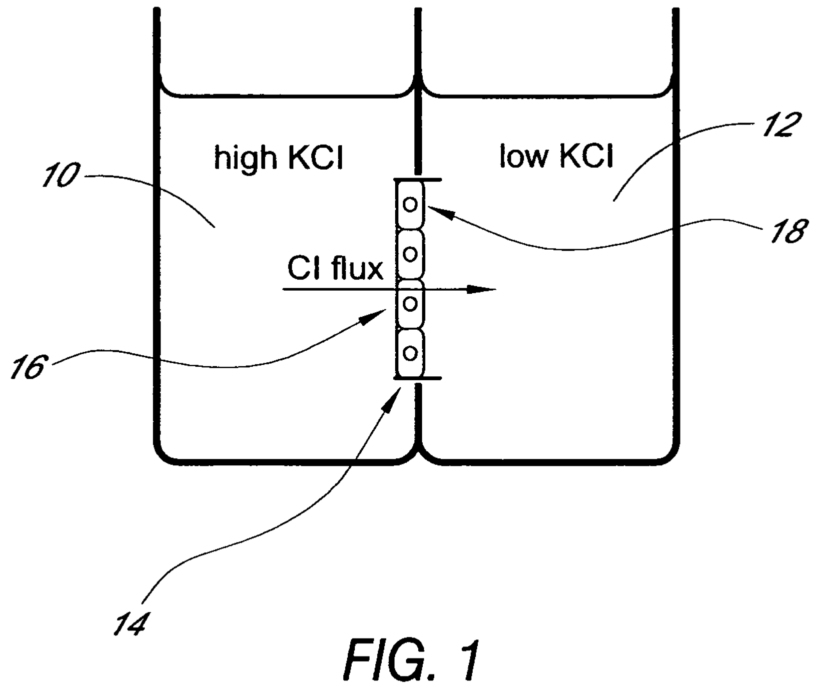
FIG. 1 is a cross section view of a typical Ussing chamber.
Figure 2:
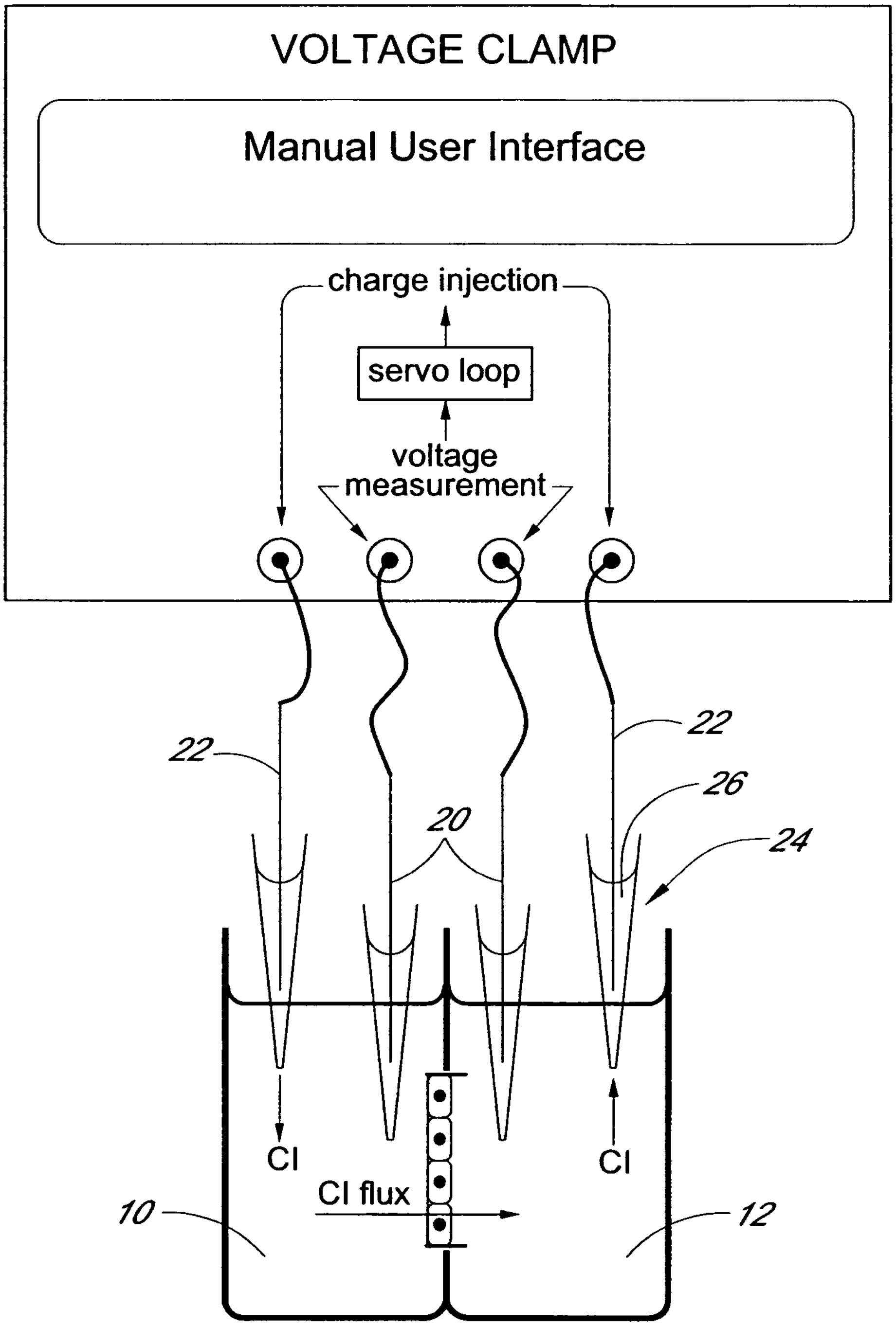
FIG. 2 is a cross section view of a typical Ussing chamber with electrode connections and a voltage clamp.
Figure 3:
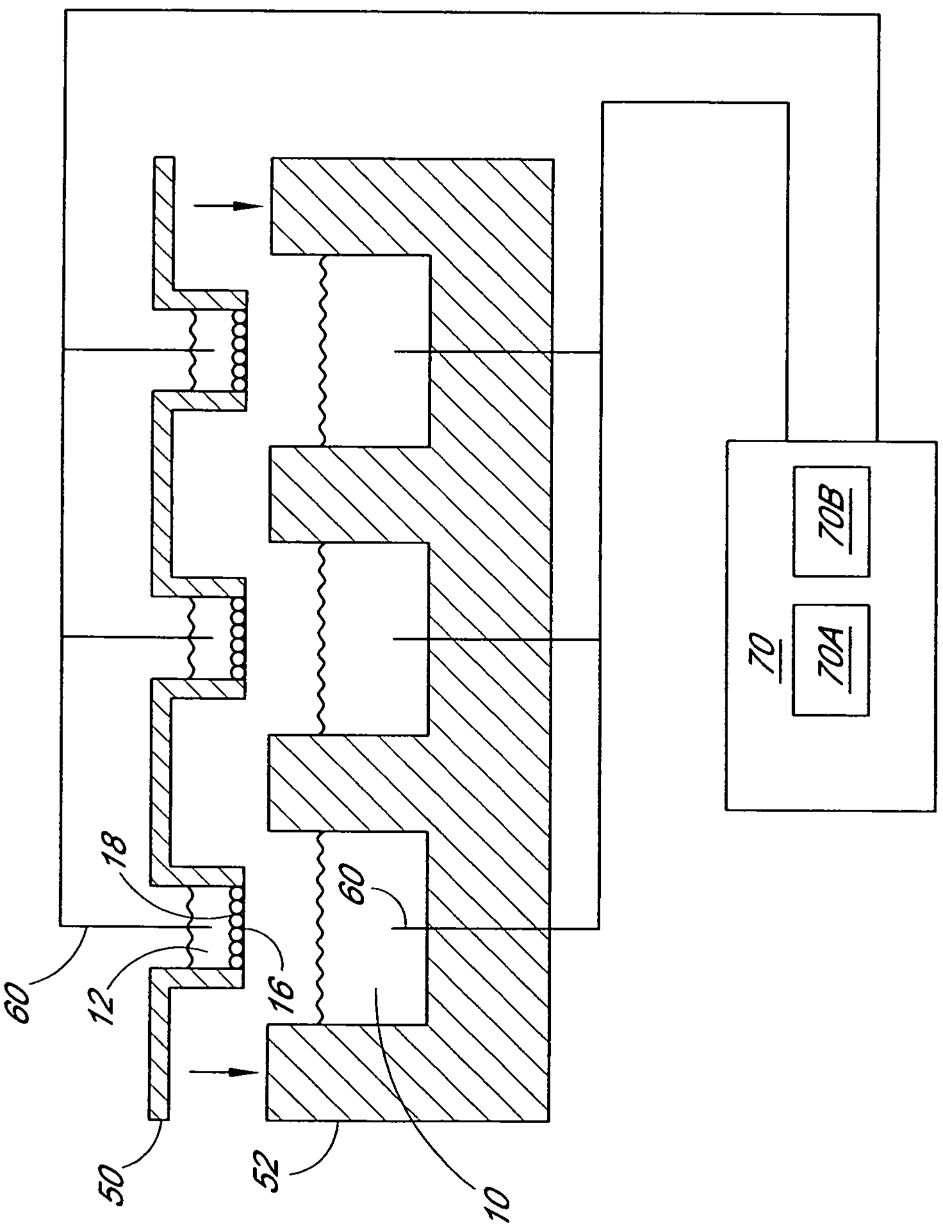
FIG. 3 is a stylized cross section of a Ussing chamber array assay system.

FIG. 3 shows a stylized cross section of one embodiment of the present invention. An upper tray 50 is positioned above a lower tray 52 so that the smaller wells of the upper tray fit into the larger wells of the lower tray. Each of the smaller wells contains a microporous membrane support 16 on the floor of the well. A confluent epithelial cell layer 18 has been grown on each membrane support 16. Alternatively, the microporous membrane support could be positioned on a sidewall of the well. The cells of the confluent epithelial cell layer advantageously contain tight junctions between them so that the intercell junctions are substantially ion impermeable.

When the upper tray 50 and lower tray 52 are brought together, a plurality of Ussing chambers is formed. As in a standard Ussing chamber, each assay chamber contains a first compartment 10 and a second compartment 12 which are separated by a cell layer 18. In this example, the upper well is the second compartment 12 and the lower well (minus the volume displaced by the upper well) is the first compartment 10. In some embodiments, the assembly process can be performed so that each Ussing chamber of the array is formed at substantially the same time as all the others. This can be achieved by the substantially simultaneous placement of the all the cell layer membranes 18 (which reside on the upper tray 50) into the wells of the lower tray 52.

Each compartment can be filled with a fluid that contains ions that will serve as a medium for ion flux across the cell layer membrane 18. The fluid, and any other desired reagents, can be added either before or after the trays are brought together to form the plurality of chambers. Adding reagents to the lower wells after the trays are brought together is easier if pre-formed holes are included in the upper tray.

Ions which are particularly useful for Ussing chamber work include sodium, potassium, calcium, bicarbonate, phosphate, and chloride. The ion concentration of the first compartment may be different than that of the second compartment. In such case, the ion gradient can thus induce an ion flux across the cell layer membrane. In some embodiments, multiple gradients can be created using more than one species of ion. An ion concentration gradient may change over time, either because ions in one compartment have moved to the other compartment, or because of chemical or biological processes occurring in a compartment that consume or generate ions. Ion concentration may also be altered by the addition of one or more reagents to a compartment. The concentrations of different species of ions can vary independently of one another. At any given time, the concentrations of a particular species of ion in the first and second compartments may be different, or may be substantially equal, depending on the requirements of the assay being performed.

As shown in FIG. 3, each compartment also contains one or more electrodes 60 which are used to induce and/or measure an ion flux across the membrane, as in a standard Ussing chamber. As depicted in FIG. 3, a particularly advantageous design is to introduce the electrodes 60 into the wells from the top and bottom. In one such embodiment, the electrodes in contact with the wells of the upper tray enter the well from the top and the electrodes in contact with the wells of the lower tray pass through the bottom of the lower tray and enter the wells of the lower tray. This can be accomplished by creating one or more openings, such as holes, in the lower tray to accommodate electrodes and then passing electrodes through, or forming electrodes in, those openings. The openings are advantageously formed so that they enter the wells of the lower tray through one of the walls of each well. The wall through which the opening passes can either be the floor of the well, or one of the sidewalls of the well. The openings can be either pre-formed (as part of an injection mold, for example), or made after the tray has been manufactured (such as by drilling, cutting, punching, or melting).

It will be appreciated that the wells of the tray, once the electrodes are inserted, should be water-tight. A fluid leak from an assay compartment can compromise the assay, require additional clean-up, and possibly damage equipment. A water-tight seal can be created by making the electrodes the exact same size as the openings to form a tight press fit, or by using a sealing agent (such as an adhesive polymer) to fill any gaps between the electrodes and the sides of the openings. A gasket or other device for creating a water-tight seal can also be used and has been found advantageous in some embodiments.

As shown in FIG. 3, the electrodes 60 can be placed in electrical contact with one or more modules 70 which are capable of control and/or data acquisition. A control module 70A can include a voltage source, and/or a current source, and a user interface that allows a user to set the parameters of the assay (such as current, voltage, time, number of samples, etc.). Voltage and/or current clamping capability can be included in a control module. The data acquisition module 70B can include one or more detectors, processors, and output devices for measuring and/or quantifying voltage, current, resistance, or other physical properties of one or more Ussing chambers in the array. Preferably, a programmable computer is used in both the control module and the data acquisition module.

It will generally be advantageous if each Ussing chamber in the array is wired separately to these modules using its own channel or group of channels so that each Ussing chamber can be controlled, and its own output monitored, independently of the other Ussing chambers in the array. One useful design that has been discovered is to use a first printed circuit board (PCB) adjacent to the upper tray and a second PCB adjacent to the lower tray. In such a design, the PCBs can be constructed so that they contain an array of electrodes which match up spatially with the array of wells on the trays. The PCB that matches the upper tray can be placed on top of the upper tray so that electrodes extend down into the wells of the upper tray. With regard to the lower tray, it is particularly advantageous to combine the lower tray with a PCB and to use electrodes that extend from the PCB, up through the bottom of the lower tray, and then into the wells of the lower tray. As above, it is advantageous to construct the lower tray electrodes assembly in a manner such that the wells of the lower tray do not leak. Accordingly, it has been found to be advantageous to fasten the lower tray and the lower tray PCB together with a gasket between them to prevent leakage.

Some embodiments of the present invention employ multiwell plates which are commercially available from companies such as Corning, Becton-Dickinson, and Millipore. Some of these plates are designed for measuring compound permeability in Caco2 assay systems. See Corning Costar Transwell Permeable Support Selection and Use Guide, Web document rev. 7/02, hereby expressly incorporated by reference in its entirety.

Figure 4:
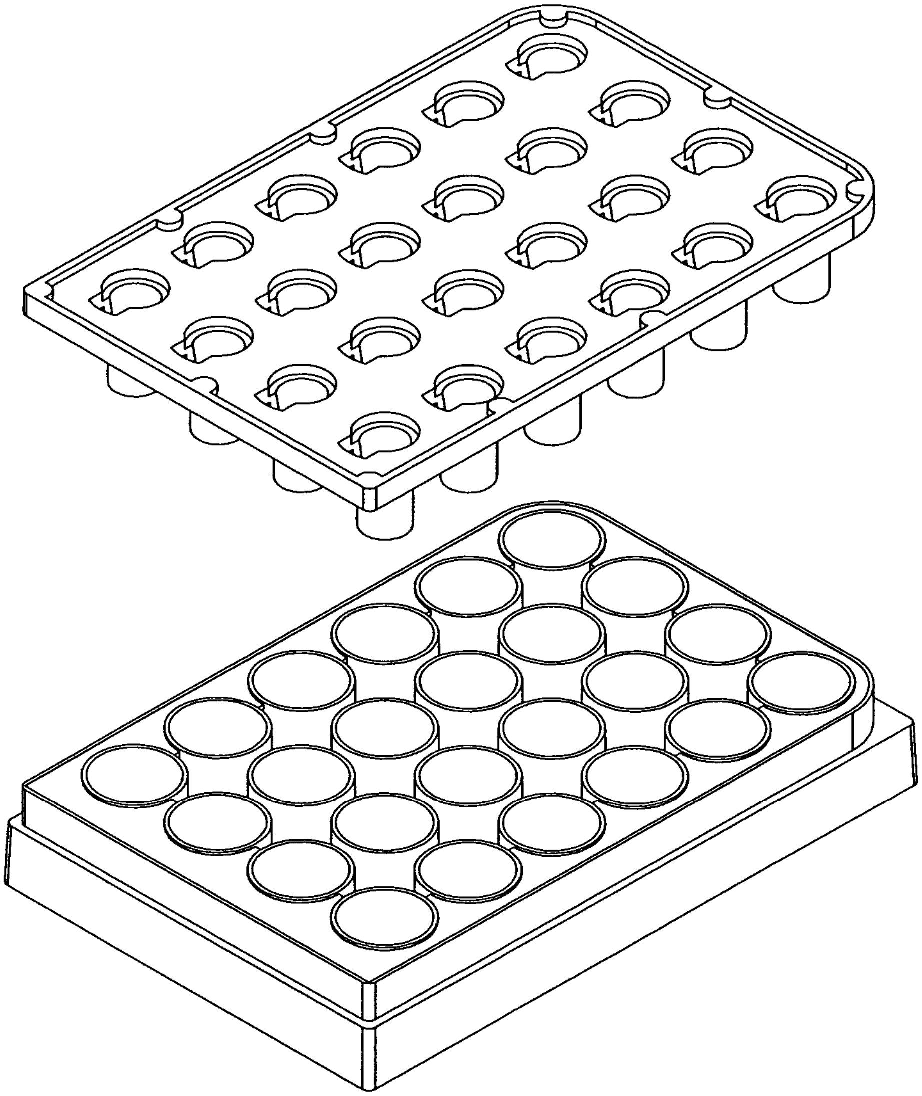
FIG. 4 is an expanded view of the bottom and middle parts of a Corning Transwell™ plate.

Some embodiments of the present invention use Transwell™ plates from Corning, the typical specifications of these particular plates are as follows. The plates have 24 wells arranged in a rectangular array of the same footprint as a standard microtiter plate. Each plate consists of three parts: i) a bottom part with 24 cylindrical wells; ii) a middle part consisting of 24 Transwells™, each of which is a cup whose bottom is a microporous membrane support on which epithelial cells can grow; and iii) a lid. FIG. 4 shows the bottom and middle parts of a Corning Transwell™ plate. The middle part also has access holes adjacent to each Transwell™ which pass through the tray to allow pipetting into and out of the bottom wells. The microporous membrane support is made of PTFE, polyester, or polycarbonate and has pore sizes ranging from 0.1 to 3 μm; the area is 0.33 $cm^2$.

Figure 5:
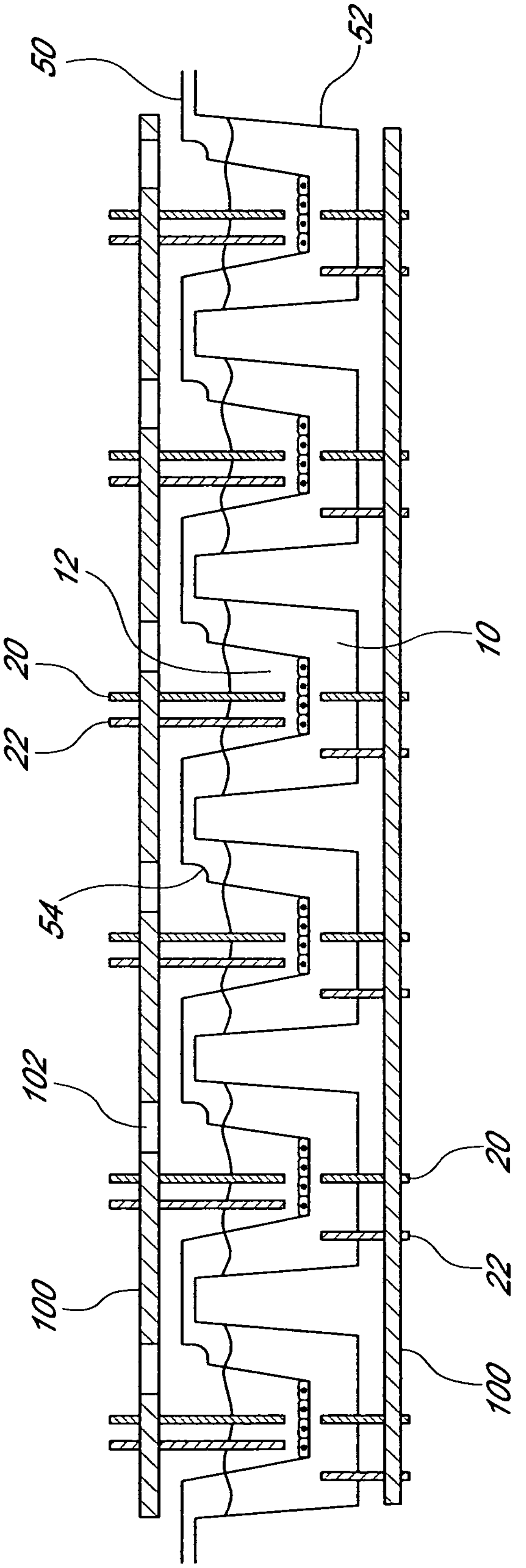
FIG. 5 is a cross section view of an Ussing chamber array constructed from a Corning Transwell™ plate.

Some embodiments of the present invention involve modifying the bottom part and middle part of a Transwell™ plate assembly so that when they are brought together, an array of Ussing chambers is formed. FIG. 5 shows a cross section of such an embodiment. The middle part of the Transwell™ assembly serves as the upper tray 50 and the bottom part of the Transwell™ assembly serves as the lower tray 52. In this design, the bottom well serves as the first compartment 10 and the Transwell™'s cup serves as the second compartment 12. The volume of the bottom well is about 1.2 mL, while that of the Transwell™'s cup is about 0.25 mL. Also shown in FIG. 5, PCBs 100 are positioned above and below the tray assembly and serve as a support for both current electrodes 22 and voltage electrodes 20. The upper PCB has access holes 102 passing through it which allows pipetting into or out of the upper well. Pipetting into or out of the lower well is enabled by access hole 102 in combination with access hole 54 which passes through upper tray 50.

The electrodes shown in FIG. 5 are bare Ag/AgCl wires rather than Ag/AgCl wires in KCl/agar-filled pipettes. In many applications, the chloride concentrations can remain constant; reagents and compounds to be added are in buffers of the same chloride concentrations as those of the initial solutions residing in the two compartments. In such a scenario, Ag/AgCl wires can be directly dipped into the solutions without needing to be "protected" by KCl/agar-filled pipettes. This means that 24 sets of simple Ag/AgCl electrodes can be fitted into the 24 miniaturized Ussing chambers of a Transwell™ plate. As shown in FIG. 5, the electrodes are mounted on two PCBs 100. The electrodes that interface with the wells of the lower tray 52 pass through holes that have been drilled into the bottom of the tray. Optionally, a soft gasket can be placed between the bottom PCB and the Transwell™ plate to prevent leakage. For construction of the PCB/electrode assemblies, bare silver rods can be soldered onto the PCBs, and silver chloride can be plated onto them using an electrolytic bath containing NaCl and HCl. For a silver rod of 1 mm in diameter and 20 mm in length, a current of 3 mA for about 20 minutes was found to be effective for the plating process. Such conditions result in a uniform and fairly tough AgCl coating of the silver surface. As the AgCl coating wears out with use, the electrodes can be re-generated with a new round of plating. Optionally, the AgCl layer can be de-plated before the re-plating process is performed.

An alternative fabrication process can be used for making electrode assemblies in KCl/agar. For example, the electrodes can be built inside a structure into which a mixture of KCl and melted agar is poured. However, the simplicity of fabrication and regeneration of bare AgCl electrodes makes their use generally preferred to that of KCl/agar.

Figure 6:
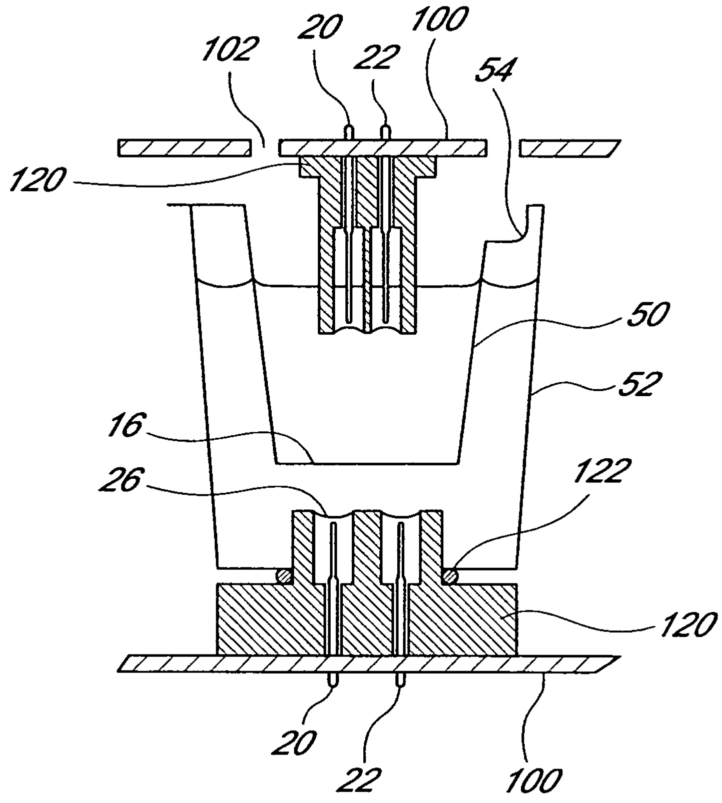
FIG. 6 is a cross section view of an Ussing chamber well containing compound electrodes.

Nevertheless, compound electrodes with KCl/agar are sometimes advantageous when the biological applications call for changes in chloride concentrations during the experiment. In such a case, a design as shown in FIG. 6 can be used. As in the agar-less design, silver rods soldered to PCBs 100 are used to create voltage electrodes 20 and current electrodes 22. However, rather than simply being introduced into the baths, the rods are first inserted into a terminal block 120. Terminal blocks are advantageously made out of a non-conducting material such as Plexiglas. The top parts of the openings into which these silver rods are inserted are enlarged so that liquefied KCl/agar 26 can be poured in. In a typical scenario, the silver rods are first electro-plated to obtain the AgCl layer. Then, hot, liquefied KCl/agar 26 is poured into the top openings in the terminal blocks 120 and allowed to gel. The assembly of the device using this configuration can be very similar to the assembly using an agar-less electrode design (FIG. 5). For the bottom electrodes, instead of drilling two holes per well, one single hole can be drilled and an O-ring 122 can be used to form the seal between the bottom part of the Transwell plate 52 and the terminal block 120. In an alternative design, thin silver wire can be used instead of 1-mm silver rods. This would allow for a much smaller electrode assembly, which would be advantageous in preparing an array having higher density. For example, smaller electrodes could be used with a 96-well plate that has the same footprint as the 24-well plate already described.

Regenerating these compound electrodes will typically require more work than regenerating their agar-less counterparts. Typically, regeneration will involve either de-soldering the electrodes from the printed-circuit board, or re-melting the KCl/agar and pouring it out of the terminal blocks. The re-melting can be achieved by dipping the electrode assemblies into hot water.

The use of a miniaturized arrangement can lead to several substantial advantages in terms of throughput, compound usage, and utility. For example, cells can be cultured simultaneously in 24 Transwells™ and 24 Ussing experiments can be run at the same time. As the area of the Transwell™ membrane support is only ⅓ that of a Snapwell™ support, fewer cells would be needed per data point; this is particularly advantageous if primary culture cells of human origin are used. Moreover, since the volumes of the bottom well and the Transwell's cup are only 1.2 and 0.25 mL, respectively, consumption of reagents and especially test compounds can be significantly reduced when compared to the 3-mL volumes of the traditional Ussing compartments. In terms of utility, the smaller surface area of the monolayer can allow more rapid voltage clamping and increased sensitivity. Standard Ussing chambers are often hampered by the poor resolution of the voltage-step activation of ion channel activity due to the large, slow capacitive current transient associated with the voltage-step command. This can be especially problematic when studying fast-activating or fast-inactivating ion channels. Miniaturizing the Ussing chamber-recording set-up can reduce this capacitive current and increase the utility of the Ussing chamber. In addition, an alternating headstage that switches between a high resistance (50 Gohm) and low resistance (50 Mohm) feedback resistor can be used to first rapidly charge the membrane followed by the high resolution recording of current flux. A capacitive-headstage amplifier can also be used, as it can rapidly charge the monolayer capacitance. Finally, circuits capable of compensating for the capacitance can be added to reduce the duration in which the output of the amplifier is saturated, during which the monolayer cannot be adequately voltage-clamped. Finally, the reduced size of the monolayer can help to reduce the background current noise, which in turn can allow for better resolution of small conductance ion channels or low channel expression levels.

Figure 7:
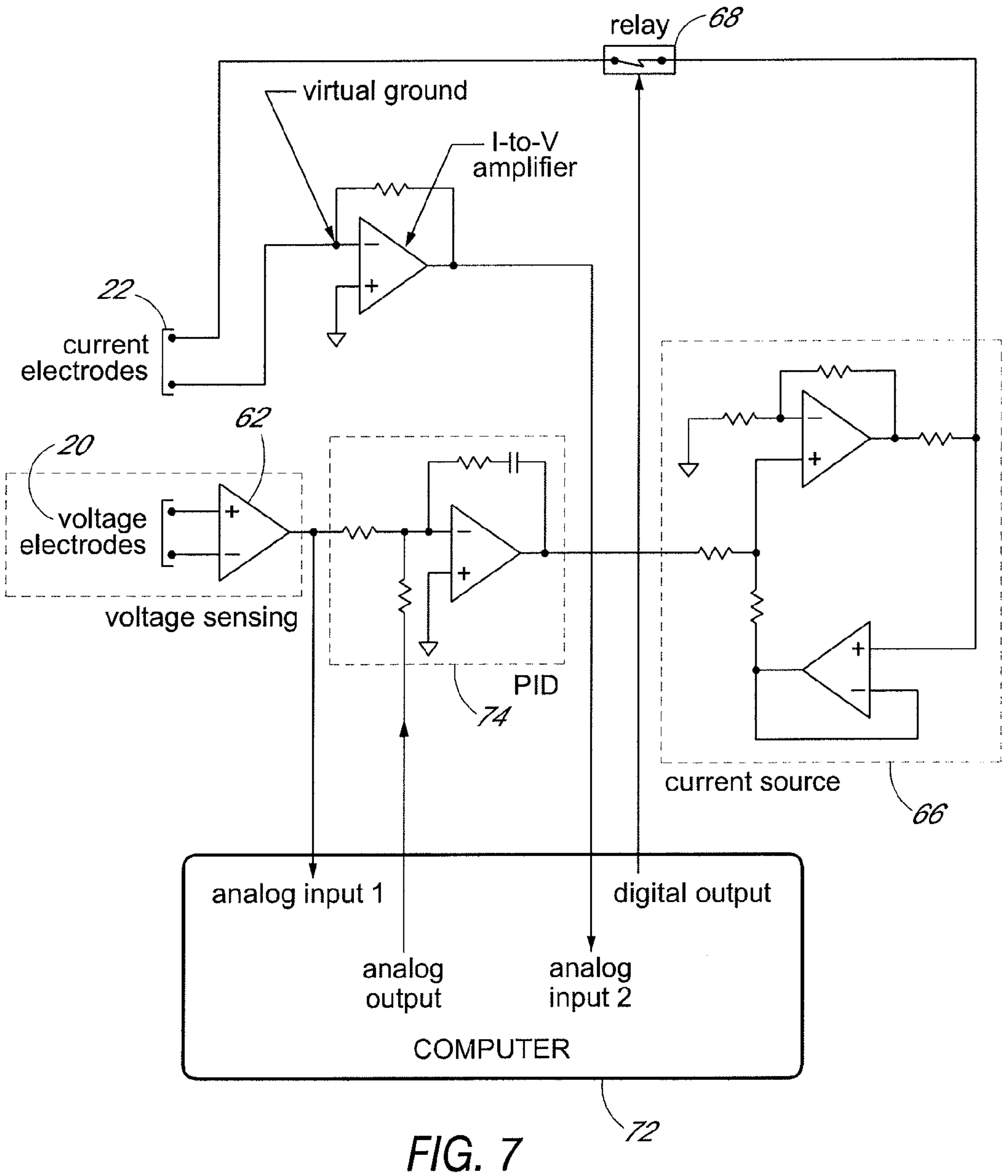
FIG. 7 is an electronic circuit diagram for a one channel of an Ussing chamber array.

For each channel, an electronic circuit as shown schematically in FIG. 7 can be used. In this configuration, the circuit is essentially a voltage sensing circuit and a current source linked together to form a PID (Proportional, Integral, Differential) servo loop. The servo loop in this particular design only performs the proportional and integral functions, but a differential function can easily be added. In this example, the PID element also serves as a summing amplifier.

It is one important aspect of this part of the system that the circuit is configured to be entirely under computer control. In contrast, control of commercially-available Ussing voltage clamps is entirely manual. User inputs are entered via front panel dials, switches, and knobs. Typically, each channel requires a 7×22 cm panel; the front panel of a state-of-the-art 8-channel voltage clamp is 60×22 cm. To set up all eight channels requires extensive of manual work; a 24-channel version would be prohibitively unwieldy.

Referring now to FIG. 7, the Ussing chamber circuit may comprise a voltage sensing differential amplifier 62 that is connected across the voltage electrodes 20 of one of the Ussing chambers. An amplifier configured as a current-to-voltage converter 64 is coupled to one of the current electrodes 22 as a current sensor, with the other current electrode 22 being connected to a current source 66 through a relay 68. A servo amplifier 74 controls the current source 66 output in response to changes in voltage across the membrane as measured by the voltage sensing amplifier 62. Circuit operation is controlled by a digitally programmable controller 72 such as a commercially available microcontroller from Motorola for example. A variety of options are available for the controller 72, as long as the controller 72 can accept analog and/or digital input signals, can store and manipulate those signals, and can produce analog and/or digital output signals in response to those input signals. General purpose computers can be configured to perform such functionality, as can integrated circuits such as the microcontrollers mentioned above as well as other integrated circuits, ASICs, programmable gate arrays, etc. It will be appreciated that the functionality described herein for the controller 72 could be split among a plurality of physical hardware devices.

In one embodiment, to set the system up, the controller 72 begins by activating the relay (via the digital output in FIG. 7) to break the servo loop. The potential $V_0$ across the cell layer is measured (via analog input 1, FIG. 7). This potential is inverted and fed to the summing amplifier of the servo amplifier 74 (via the analog output, FIG. 7). The output of the servo amplifier is thus made zero and no current is produced by the current source 66. The relay contact is now re-established to reinstate the servo loop. If nothing is done to the cell layer and no chloride flux flows across it, the circuit remains quiescent with no current being produced by the current source. Any changes in the cell layer's chloride permeability will cause chloride flux and a change in potential, which will show up at the output of the servo amplifier 70, causing the current source to react. This reaction brings the potential across the cell layer back to its original value $V_0$. The cell layer is thus “clamped” at $V_0$. The current needed to maintain $V_0$ across the cell layer is monitored via analog input 2 of the controller 72, which receives the output of the current to voltage converter 64. With this digitally programmable controller based design, setting up the chambers can be completely automated. In the multi-chamber assay embodiment, a plurality of circuits as shown in FIG. 7 are provided (24 of them in one embodiment, for example), and the controller 72 has 24 separate I/O channels, one of which is shown in FIG. 7. In this embodiment, the controller 72 measures the 24 initial $V_0$ potentials and sets the 24 clamps; although the user may be allowed to retain the option to modify these clamping voltages if necessary. Data acquisition can also be performed by the controller 72. In some embodiments, an experimental protocol will call for voltage pulses to be periodically applied across the cell layer and the resulting current to be measured to assess the layer's electrical resistance; these pulses can be biphasic. The circuit described above is capable of such operation. As the clamp voltage $V_0$ is produced by the computer (via the analog output, FIG. 7), it can periodically superimpose on this voltage a biphasic pulse of amplitude and duration of the user's choosing. Any detectable change that is induced by the biphasic pulse can be used to determine the cell layer's electrical resistance, which can be calculated according to Ohm's law. The frequency response of this circuit is 10 kHz; the minimum cell layer potential that can be measured is about 10 μvolt.

Manual Ussing voltage clamps can also produce periodic voltage pulses to test the cell layer's electrical resistance; these voltage pulses can be biphasic. This can be achieved by adding a pulse generator whose output is added to the clamp voltage. This generally adds complexity to the circuitry and requires additional manual knobs and dials on the front panel that the user has to manipulate. In some embodiments of the present invention, however, these periodic test pulses are produced by the same digital-to-analog circuitry that the computer uses to set the clamp voltage.

In some embodiments, the controller 72 is provided with a display and user input devices such as a keyboard and mouse to control the sensing and driving circuits as shown in FIG. 7 and to display stored and/or mathematically processed data from the Ussing chamber electrodes. The graphical user interface of the present computer-controlled 24-channel voltage clamp and its automated setup capability are improvements over the current state of the art.

It is possible to use manual pipettes to add and remove fluids from a 24-Transwell™ plate. However, there are at least two advantages of an automated pipetter that are worth considering. First, a typical plastic disposable pipette tip is quite large when compared to the size of a well when using 24-well Transwell™ plates since the electrodes will take up some room. To avoid disturbing the cell layer, it is generally advantageous to pipette against the side of the well, and not directly onto the layer. Such a procedure is very difficult using disposable pipette tips because of mechanical clearance problems. Second, even though most Ussing work produces slow signals on the order of tens of minutes, it is still best to synchronize all 24 channels so that well-to-well comparison is not undermined by issues such as differential aging of cell samples. Manual pipetting does not allow synchronous addition of reagents to all 24 wells.

Figure 8:
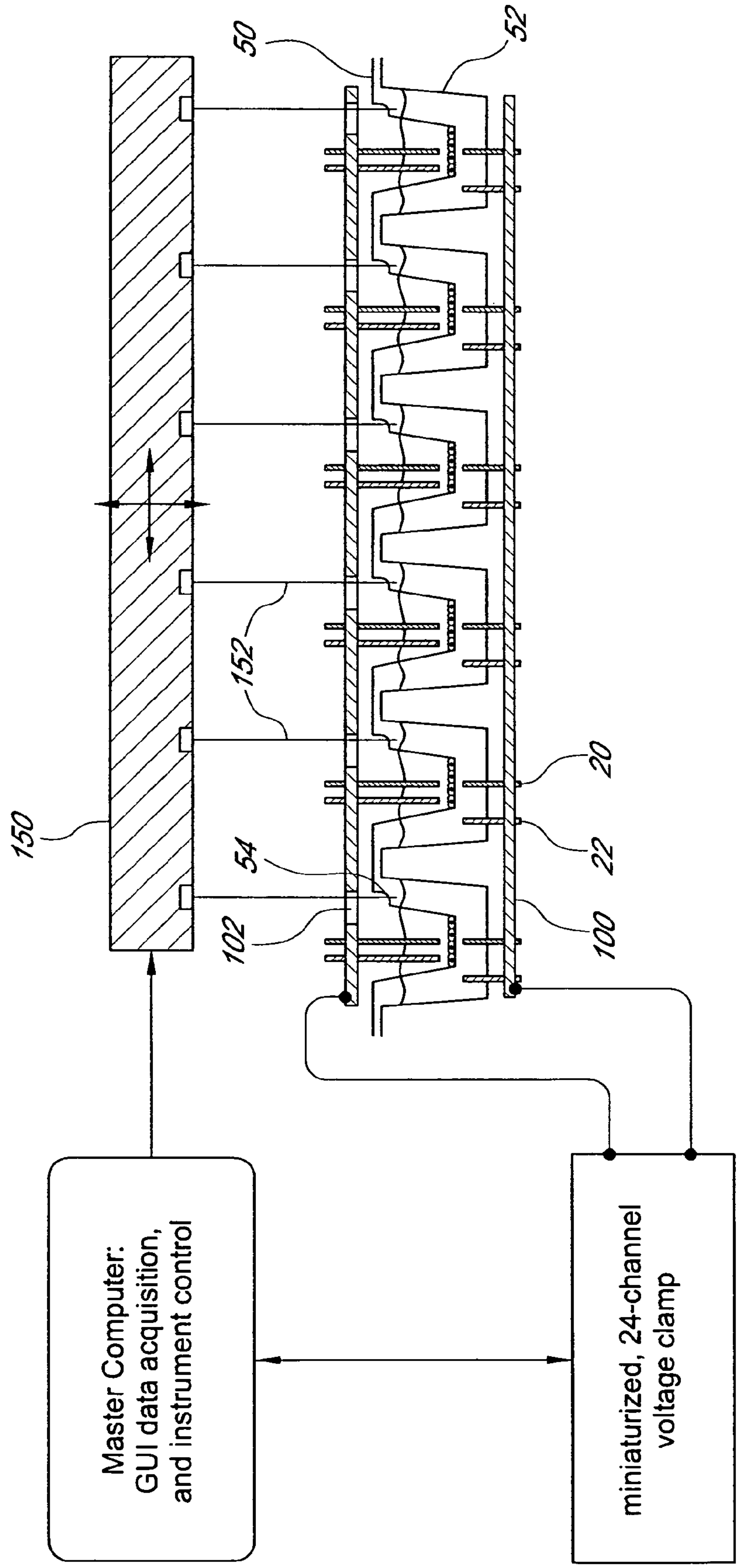
FIG. 8 is a cross section view of an Ussing chamber array coupled to an automated pipetter.

Accordingly, some embodiments of the present invention utilize an automated pipetter. FIG. 8 shows a schematic of such an automated pipetter 150 in combination with a 24-well Ussing array. The automated pipetter 150 is advantageously a 24-channel pipetter fitted with thin, Teflon coated needles 152 instead of bulky plastic pipette tips. The reagents can be delivered through access holes 102 and 54. Because of the small diameter of the needles 152, reagents can be introduced into the well along its sloping side. Since the wells of a Transwell™ plate are conical in shape, this avoids direct jetting of the liquid onto the cell layer. Further, since pipetting can be computer controlled, the dispensing speed can be varied to be as gentle as possible. Advantageously, the automated pipetter is motorized and is capable of moving in three dimensions to position the needles in or above the appropriate wells. Finally, all 24 chambers can be addressed simultaneously so that all 24 signals are synchronous.

The miniaturization strategy outlined here can be extended to higher densities. Transwell™-type plates also exist in 96-well format. Since the Ag/AgCl electrodes can be very thin metallic wires, they can be made small enough to fit into the wells of a 96-well plate. An automated liquid-handling device would also be advantageous at this density since manual pipetting can be a major source of human error. One main advantage of a 96-well Ussing chamber is higher throughput. In addition to that, however, higher density also leads to a further reduction in cell and reagent consumption. There would also be a significant reduction in the capacitance of the cell layer, which could allow for faster electrical kinetics.

It is also possible to use one pair of electrodes for both voltage measurement and current injection. In this scenario, the electronics circuit quickly switches the electrodes from the voltage sensor to the current source and back. With an analog switch, this can be done quickly enough to maintain a frequency response of 5-10 KHz. An advantage of this is that instead of four electrodes, only two will be needed, which considerably reduces the required mechanical clearance. This would open up the possibility of using 384-well or even higher density plates to perform Ussing experiments. Reducing the size of the monolayers by miniaturization can also help to reduce the capacitance of the cell layer allowing for faster signals to be detected. Further, instead of clamping the voltage across the cell layer, it is also possible to clamp the current. For example, as the current that flows across the cell layer changes because the layer's resistance changes, a current of the appropriate size and polarity can be injected to restore the total current to its initial value. The injected current reflects the resistance change undergone by the cell layer. Again, such a circuit can be computer-controlled.

Some embodiments of the present invention have broad utility for functional analysis of ion transport proteins in both basic research and pharmaceutical drug discovery using a variety of cell types. Basic research applications can include elucidation of biological mechanisms underlying normal function and disease states. Pharmaceutical applications can include screening of test compounds for both effects on specific transport proteins or general epithelial cell function. Functional analysis can be performed on cellular transport proteins, including ligand-gated channels (such as $P_2X$, NMDA, GluR, and Ach), second-messenger operated channels (such as CFTR), voltage-gated channels and electrogenic transporters and pumps. For ligand-gated channels, the automated pipetter can be used to quickly and simultaneously add ligands to all 24 (or more) chambers to control the channels. Voltage-gated channels can be opened by rapidly changing the clamping voltage so as to cause channel opening and current flow. For some types of work, a 1-KHz frequency response of the circuit may not be sufficient to detect certain types of fast current changes. In such cases, however, the electronic design can be optimized to obtain a 10-fold improvement to permit such detection. In some embodiments, the same instrument can be used for both of these modes of action. Some embodiments of the present invention can also be used to study the response of epithelial cell cultures to other signaling molecules such as peptides and proteins acting through receptors or signaling pathways. For example, epithelia are known to regulate ion transport in response to various stimuli including inflammatory mediators. See Danahay, H et al., Interleukin-13 induces a hypersecretory ion transport phenotype in human bronchial epithelial cells. *Am. J. Physiol* (*Lung*) 282:L226-L236, 2002, which is hereby expressly incorporated by reference in its entirety. Some embodiments of the present invention can be used to study the response of the epithelial monolayer. For example, agents known to damage or stress cells would be expected to cause a loss of integrity of the monolayer, which would be detected as a decrease in resistance. See Duff, T et al., Transepithelial resistance and inulin permeability as endpoints for in vitro nephrotoxicity testing. Altern Lab Anim. 30 Suppl 2:53-9 (2002), which is hereby expressly incorporated by reference in its entirety.

EXAMPLE 1

Testing the Ussing Array

Utility of the Ussing array was demonstrated using a Fischer Rat Thyroid (FRT) epithelial cell line expressing a mutant form of the CFTR (*Cystic Fibrosis Transmembrane Regulator*) gene. CFTR encodes a protein kinase A-regulated chloride channel called CFTR (cystic fibrosis transmembrane regulator). Mutations in CFTR result in defective expression and/or function of the CFTR protein and result in cystic fibrosis. A high-throughput assay for CFTR function in epithelial cells is of interest for testing compounds that could improve the expression and/or function of CFTR. FRT cells engineered to carry the mutant ΔF508-CFTR in their membranes were grown on the microporous supports of 24-Transwell™ plates.

Figure 9:
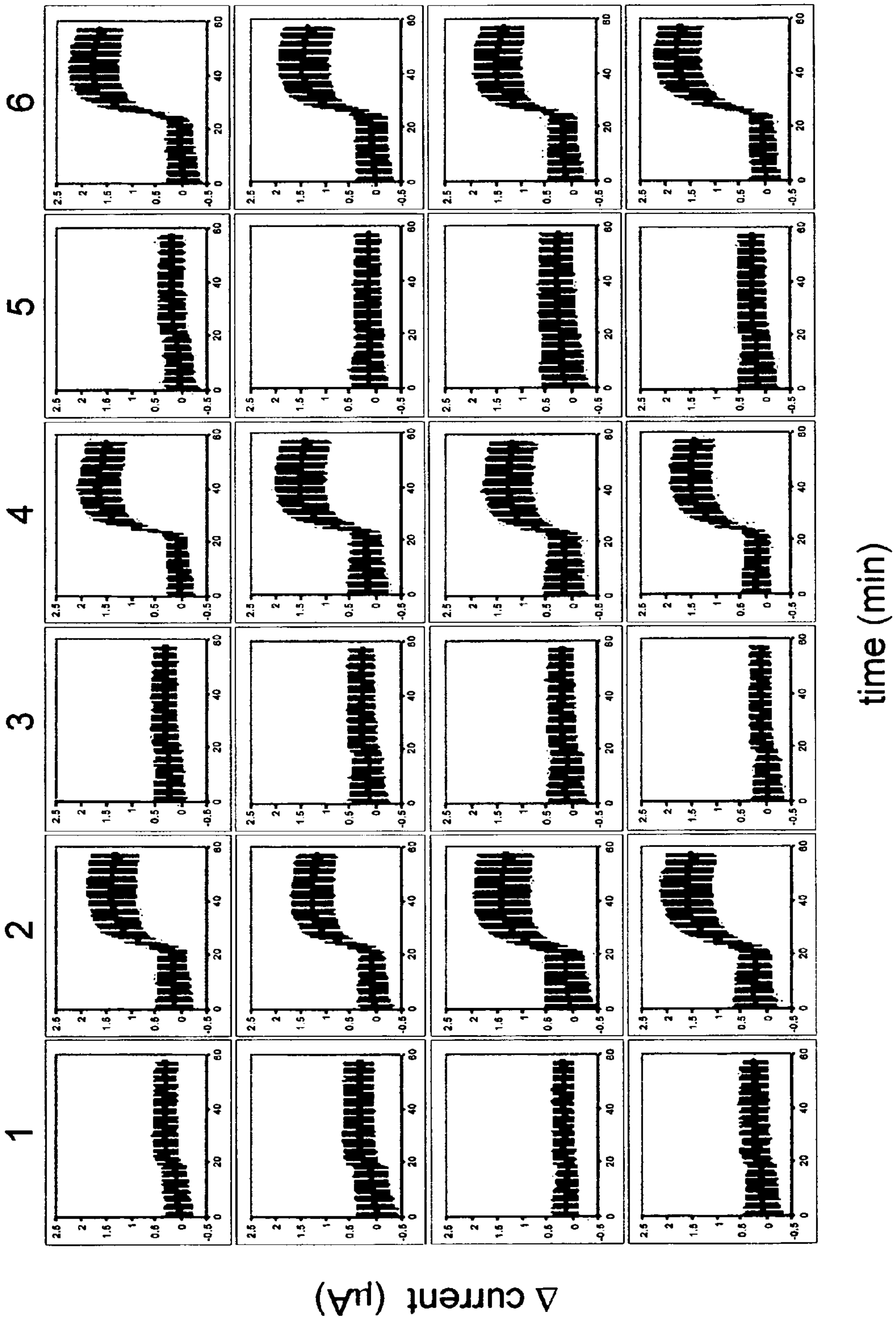
FIG. 9 shows the results of an experiment performed to test the response uniformity between the wells of an Ussing chamber array.

FIG. 9 shows the results of an experiment performed to test the response uniformity between wells. The clamp voltage was set at 60 mV; ±10 mV test voltage pulses were applied every minute to monitor the resistance of the cell layer. 20 μM forskolin and 100 μM genistein were added to columns 2, 4, and 6 while only DMSO was added to columns 1, 3, and 5 as controls. The change in current elicited with forskolin and genistein was 1.37±0.20 μA while with DMSO, it is only 0.11±0.04 μA. The current full-scale is 3 μA.

Figure 10:
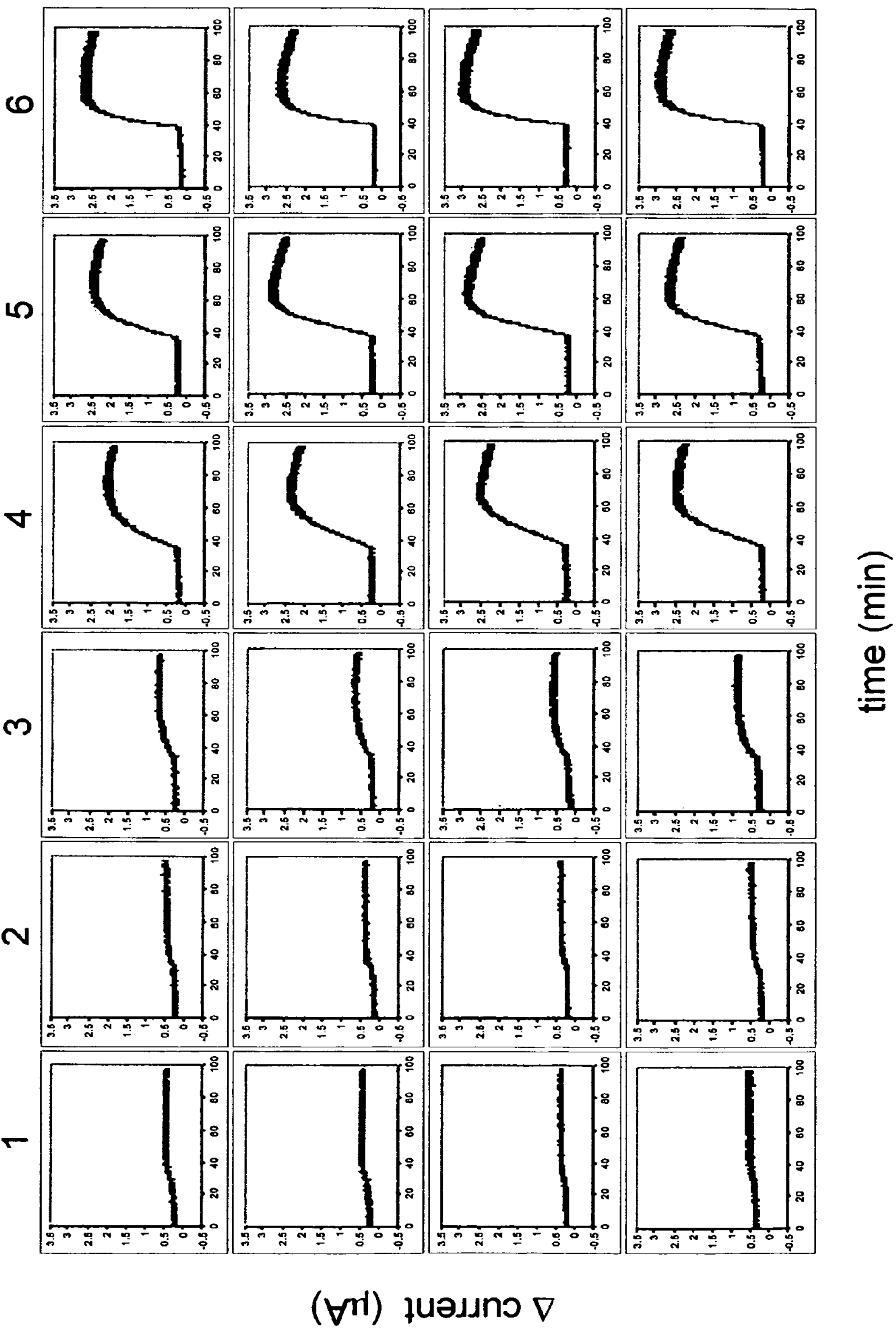
FIG. 10 shows the results of a dose response experiment.
Figure 11:
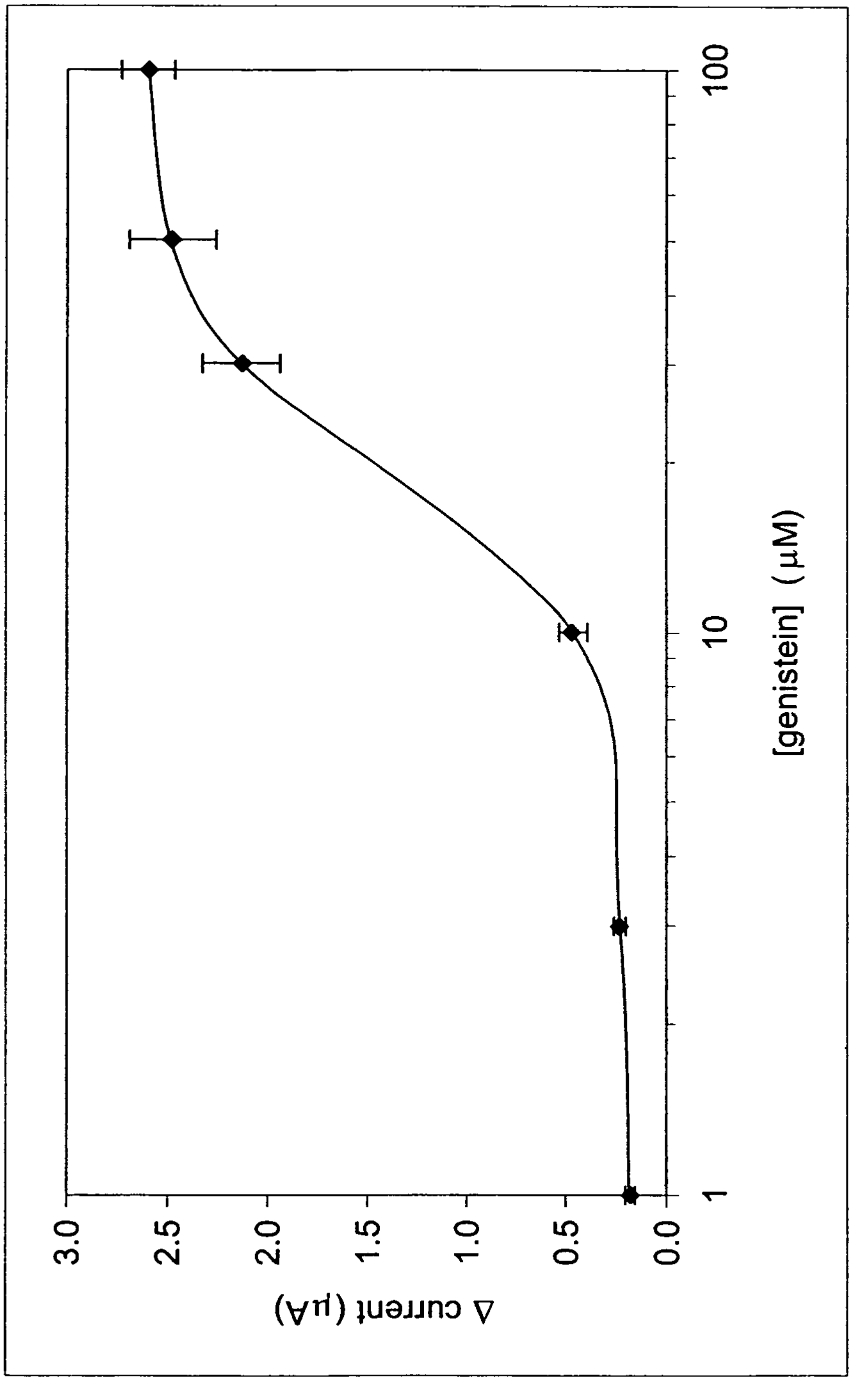
FIG. 11 shows detected current plotted as a function of genistein concentration in a dose response experiment.

FIG. 10 shows a dose-response experiment. The clamp was set at 60 mV. FRT cells carrying ΔF508-CFTR were incubated for 48 hours at 27° C. prior to the experiment in order to enhance the correct folding of the mutated CFTR protein. 20 μM forskolin was added to all wells. 1, 3, 10, 30, 50, or 100 μM genistein were added to columns 1 through 6, respectively. The current full-scale is 4 μA. In FIG. 11, the increase in current is plotted as a function of added genistein, giving an EC-50 response of 18.1±0.8 μM (n=4); the published value is 14.8±3.8 μM (n=47); The error bars come from the four data points obtained from each genistein concentration.

This experimental setup using a 24-Transwell™ plate, bare Ag/AgCl electrodes, and computer-controlled voltage clamp produces experimental results that are identical in most aspects to those obtained with a traditional Ussing chamber driven by a manual voltage clamp. One noteworthy difference, however, is the amplitude of the current increase. The increase is only one third of that obtained from a traditional Ussing chamber. This is expected, however, since the cell layer area used with the Transwell™ (0.3 $cm^2$) is about one third of the cell layer area in a traditional Ussing chamber (1.1 $cm^2$). Taken together, the two experiments shown here demonstrate that this novel high-throughput Ussing technology will be useful for both screening the activities of compounds, and ranking their potencies.

What is claimed is:

1. An assay apparatus comprising:

a first multiwell plate having a plurality of wells, each well having a top opening and a bottom panel;

a second multiwell plate having a plurality of wells having top openings, wherein the plurality of wells are aligned with the plurality of wells of said first multiwell plate and are dimensioned such that the plurality of wells on said second multiwell plate fit into the top openings of the plurality of wells of said first multiwell plate to create a pair of adjacent multiwell plates forming dual-compartment wells;

each of said dual-compartment wells comprising a cell layer membrane separating two compartments of each dual-compartment well;

a pair of printed circuit boards sandwiching said pair of adjacent multiwell plates; a first set of electrodes extending into the plurality of wells of said first multiwell plate, wherein said first set of electrodes extend through said bottom panel of said plurality of wells of said first multiwell plate;

a second set of electrodes extending into the plurality of wells of said second multiwell plate, wherein said second set of electrodes extend through said top openings of said plurality of wells of said second multiwell plate, wherein said first and second electrodes extend from each of said printed circuit boards and into at least some of said dual-compartment wells; and a multi-channel digitally programmable electronic control and sensing circuitry configured to substantially simultaneously apply signals to at least some of said electrodes and sense signals from at least some of said electrodes.

2. The assay apparatus of claim 1, wherein said dual-compartment wells are formed as an array of first compartments and a respective corresponding array of mating second compartments.

3. The assay apparatus of claim 1, wherein some of said electrodes extend in substantially opposite directions.

4. The assay apparatus of claim 1, additionally comprising digitally controlled amplifier electronics coupled to said array of electrodes for applying and receiving electrical signals to and from said electrodes.

5. A method of characterizing the biological activity of a candidate compound comprising:

providing the apparatus of claim 1;

exposing one or more cells of said cell layer membrane of claim 1 to said candidate compound; and monitoring an electrical property with said multi-channel digitally programmable electronic control and sensing circuitry, wherein said property is indicative of a biological activity of said compound.

6. The method of claim 5, wherein said property is electrical current.

7. The method of claim 5, wherein said property is electrical potential.

* * * * *